(12) United States Patent
Lukenbach et al.

(10) Patent No.: US 6,540,986 B2
(45) Date of Patent: Apr. 1, 2003

(54) SUNSCREEN COMPOSITIONS

(75) Inventors: Elvin R. Lukenbach, Flemington, NJ (US); Curtis Cole, Langhorne, PA (US); Prakash Naik-Satam, Bloomfield, NJ (US); Ralph Stutzman, San Antonio, TX (US)

(73) Assignee: Johnson & Johnson Consumer Products, Inc., Skillman, NJ (US)

( * ) Notice: Subject to any disclaimer, the term of this patent is extended or adjusted under 35 U.S.C. 154(b) by 14 days.

(21) Appl. No.: 09/755,918

(22) Filed: Jan. 5, 2001

(65) Prior Publication Data

US 2001/0001659 A1 May 24, 2001

Related U.S. Application Data

(63) Continuation of application No. 08/495,734, filed on Jun. 8, 1995, now abandoned.

(51) Int. Cl.$^7$ .............................. A61K 7/42; A61K 7/44; A61K 7/00; C09C 1/36; C01G 23/047
(52) U.S. Cl. ..................... 424/59; 106/436; 423/610; 424/60; 424/400; 424/401
(58) Field of Search .................. 424/59, 60, 400, 424/401; 423/610; 106/436

(56) References Cited

U.S. PATENT DOCUMENTS

| | | | |
|---|---|---|---|
| 5,028,417 A | * 7/1991 | Bhat et al. ................... | 424/59 |
| 5,032,390 A | 7/1991 | Iwaya et al. | |
| 5,188,831 A | * 2/1993 | Nicoll et al. ................ | 424/401 |
| 5,207,998 A | 5/1993 | Robinson et al. | |
| 5,340,567 A | * 8/1994 | Cole et al. ................... | 424/59 |
| 5,605,678 A | 2/1997 | Ascione et al. | |
| 5,616,331 A | 4/1997 | Allard et al. | |
| 5,980,871 A | 11/1999 | Lukenbach et al. | |

FOREIGN PATENT DOCUMENTS

| | | |
|---|---|---|
| DE | 3642794 | 7/1991 |
| EP | 535972 B1 | 4/1995 |
| EP | 628303 B1 | 9/1997 |
| EP | 619999 B1 | 1/2001 |
| WO | WO 90/06103 | 6/1990 |
| WO | WO 90/11067 | 6/1990 |
| WO | WO 93/11742 | 6/1993 |
| WO | WO 94/04131 | 3/1994 |

OTHER PUBLICATIONS

Tioveil Formulation, 5 pp. (available prior to Jun. 1995).
Hewitt, Julran, P. "Titanium Dioxide: a Different Kind of Sunshield", DCI 26–32, (Sep. 1992).
Dahms, Gerd H., "Formulating With A physical Sunblock", Cosmetics and Toiletries, vol. 107 (Oct. 1992).
Brochure published by Tioxide Co., (1992).
Four SUNDOWN* brand sunscreen formulations marketed in the United States from 1990 to 1997: SPF 4, SPF 8, SPF 15, and SPF 30.
Cole, et al., In Vitro Model for UVB and UVA Photoprotection, in Lowe, et al, *Development, Evaluation and Regulatory Aspects*, pp. 395–404 (1990).
"Sunscreen drug products for over–the–counter human drugs", Federal Register, pp. 38206–38269 (Aug. 25, 1978).
English Abstract –German Patent—DE3642794 A1 (1991).
English Abstract –Japan Patent—JP90022724 (1990).
PCT Search Report, PCT/US96/09380.

* cited by examiner

*Primary Examiner*—Shelley A. Dodson
(74) *Attorney, Agent, or Firm*—Michele G. Mangini; Andrea L. Colby

(57) ABSTRACT

This invention relates to novel sunscreen compositions containing inorganic sunscreen agents, anionic emulsifiers and an oil component which permit the use of high amounts of inorganic sunscreen agents in the compositions without having extreme whitening effects and achieving high sun protection factors.

14 Claims, No Drawings

US 6,540,986 B2

SUNSCREEN COMPOSITIONS

This application is a continuation of Ser. No. 08/495,734, filed Jun. 8, 1995, now abandoned.

FIELD OF THE INVENTION

This invention relates to new and useful ultraviolet radiation sunscreen agents and compositions displaying enhanced protection and to methods of protecting human skin against the potentially harmful effects of sunlight.

BACKGROUND OF THE INVENTION

Although a tan has long been considered a status symbol indicative of good health and the ability to secure sufficient leisure time to enjoy outdoor activities such as swimming, tennis, golf, skiing and the like, it has become very evident that excessive exposure of the human skin to sunlight is harmful.

It is well documented that human skin is sensitive to sunlight and artificial light containing radiation of wavelengths between about 290 nanometers (nm) and 400 nm. Ultraviolet radiation of wavelengths between about 290 nm and 320 nm (UV-B region) has been known to rapidly produce damaging effects on the skin including reddening or erythema, edema, blistering or other skin eruptions in more severe cases. Prolonged or chronic exposure to radiation in this wavelength range has been associated with serious skin conditions such as actinic keratoses and carcinomas. In recent years, concern has also been expressed regarding ultraviolet radiation of wavelengths above 320 nm (UV-A region) and the adverse effects of such radiation on human skin. The radiation between 320 and 400 nm also contributes to the premature aging of the skin. In addition, recent studies indicate that chronic sun exposure limits the immuno-response of the skin. There is also evidence that a tan will offer some protection against burning but is quite ineffectual against other types of solar damage.

Growing public awareness that the enjoyment of outdoor activities must go hand in hand with adequate sun protection has led to an unprecedented growth in the area of sunscreen products. A desirable sunscreen product should have the following attributes: protection in both the UV-A and UV-B ultraviolet radiation ranges; maintenance of coverage, i.e., waterproof and perspiration proof; application and use convenience, i.e., ease of application, invisibility, non-staining and non-greasy; and freedom from irritation as a result of its ingredients, in particular, its active sunscreen ingredients. Of recent interest in this area have been some concerns over the irritancy and sensitization problems that may occur in some individuals utilizing sunscreen products with high SPF values containing organic sunscreen agents.

The effectiveness of a sunscreen product is indicated by its sun protection factor (SPF). The sun protection factor is the ratio of the amount of exposure (dose) required to produce a minimal erythema reaction in protected skin to the amount required to produce the same reaction in unprotected skin. The absolute dose differs from person to person and is largely dependent on one's genetic predisposition and ethnic origin. If a person would normally require ten minute exposure to sunlight to develop a minimal erythema reaction, this person when using an SPF 15 sunscreen product should be able to tolerate up to 150 minutes of sunlight without an erythema reaction. Recent public awareness of the problems of exposure to sunlight has led to a demand for sunscreen products with high SPF values, i.e., at or above SPF 8.

Ease of application and cosmetic appeal, on the other hand, are important in formulating sunscreen compositions. These characteristics rely on subjective evaluations such as visual and tactile impression by the user. Consumer research studies indicate that a sunscreen formulation should rub in easily, leave the skin non-sticky and, above all, should be invisible on the skin after application. Sunscreen compositions containing organic sunscreen agents have been found, in some cases, to be irritating to the skin. Therefore, use has been made of inorganic sunscreen agents, such as titanium dioxide and zinc oxide.

For example, Japanese Patent Application No. 1981-161, 881, describes cosmetics containing 0.1–40% of ultrafine divided titanium oxide with a particle size of 10–30 nanometers (nm) which has been rendered hydrophobic. It indicates that when hydrophobically treated titanium oxide with a particle size of 10–30 nm is blended into cosmetic base materials, it transmits visible light but reflects and scatters the harmful ultraviolet rays. It has been found that when titanium dioxide of this particle size range is utilized as a sunscreen agent in sunscreen compositions, it may result in the loss of one of the most desired properties of such compositions, i.e., invisibility.

U.S. Pat. No. 5,028,417, issued Jul. 2, 1991, describes sunscreen compositions containing microfine titanium dioxide. The particle size of the titanium dioxide is required to be less than 10 nm. It also states that other sunscreen agents can be utilized with the titanium dioxide.

U.S. Pat. No. 5,340,567, issued Aug. 23, 1994 describes a sunscreen composition comprising a synergistic combination of titanium dioxide having a particle size of less than about 35 nm and zinc oxide having a particle size of less than about 50 nm with titanium dioxide and zinc oxide being present at given ratios.

German Patent No. 3,642,794 (1987) describes a cosmetic composition for preventing sunburn which contains 1–25% zinc oxide of a particle size of 70–300 microns. It further indicates that the composition may also contain titanium dioxide of a particle size of 30–70 microns. This composition is undesirable due to its unaesthetic whiteness characteristics at high SPF levels.

U.S. Pat. No. 5,188,831, issued Feb. 23, 1993, describes sunscreen compositions wherein the sunscreen effect is obtained from a blend of oil-dispersible ultrafine titanium dioxide and water-dispersible titanium dioxide. However, the SPF level obtained is only of 10 with a total concentration of titanium dioxide of 5.0% w/w.

World Patent Application WO 90/06103, published Jun. 14, 1990, describes titanium dioxide sunscreens where the microfine titanium dioxide particles are coated with a phospholipid, either through the use of a powder mill or through the making of a dispersion in an oil phase containing the phospholipid with a high shear mixer. The phospholipid coated titanium dioxide is then incorporated into sunscreen compositions. A high efficiency is claimed: the data presented shows SPF values of up to 11 for a 3.75% titanium dioxide concentration and up to 25 for a 7.5% concentration of titanium dioxide. The use of high shear mixer or a powder mill is a complicated and energy intensive process.

EP 535972 A1, published Apr. 7, 1993 describes a method of preparing sunscreens in which a dispersion of zinc oxide and/or titanium dioxide particles in an oil is formed by milling.

EP 619999 A2, published Oct. 19, 1994 describes an aqueous dispersion of particulate metallic oxide of particle size less than 200 nm mixed with an emulsifier and an oil phase and also an organic hydrophobic sunscreen to form an o/w emulsion. The resulting sun protection composition has a higher SPF than would be expected if there was only an additive effect. However, the titanium dioxide alone at 4% yielded a SPF of only 7 to about 11.

EP 628303, published Oct. 19, 1994 describes a process for preparing a sunscreen composition. It consists of mixing sunscreen particles of metallic oxide less than 200 nm dispersed in an oil with one or more emulsifier and/or organic sunscreens. The resulting sunscreen composition is claimed to have a SPF value considerably higher than expected. The high SPF is only obtained when a metallic oxide is blended with an organic sunscreen. In fact, when no organic sunscreen is used, the SPF value is only about 7.

WO 93/11742 describes sunscreen compositions comprising titanium dioxide and iron oxide of particle less than 200 nm preferably coated with a phospholipid.

An article published in DCI in September 1992 by Tioxide Specialties Ltd. describes various ways of incorporating oil or water dispersions of titanium dioxide in emulsions. However, no data is given on the resulting SPF values.

An article published in Cosmetics and Toiletries, Vol. 107, October 1992, describes various ways of formulating with a physical sunblock. The discussion focusses on using titanium dioxide in a dispersion or using an emulsifier which is also an effective dispersing agent for titanium dioxide. It states that SPF's far above 20 can be achieved. However, no examples are given, nor does the article mention the specific sunscreen components or their compositions.

A brochure published by the Tioxide Company on Mar. 15, 1994, discloses organic sunscreens of high SPF values obtained without the addition of any organic sunscreens. When measured, the SPF of the sunscreen compositions was indeed that described. However, when the titanium dioxide concentration was measured, it was at least twice what was claimed.

OBJECTS OF THE INVENTION

It is, therefore, an object of the present invention to provide improved sunscreen agents and compositions.

It is another object of the present invention to provide sunscreen compositions containing sunscreen agents that overcome the disadvantages of heretofore available materials and provide adequate and safe protection for human skin.

It is a further object of this invention to provide methods of protecting human skin against the harmful effects of sunlight.

These and other objects and features of the present invention will become readily apparent to one skilled in the art from the detailed description given hereinafter.

SUMMARY OF THE INVENTION

The foregoing objects and other features and advantages of the present invention are achieved by sunscreen compositions containing inorganic sunscreen agents as the active ingredients. More particularly, the present invention relates to sunscreen compositions containing titanium dioxide and zinc oxide of preferred particle size ranges, of preferred coating and in preferred amounts and ratios as the sunscreen agents. These specific compositions permit the use of much lower amounts of the sunscreen active ingredients than previously achievable while still achieving the desired high SPF values for the compositions and without the unsightly whiteness which occurs in prior sunscreen compositions at concentrations above about 5%. In the sunscreen compositions of this invention, considerably higher concentrations of titanium dioxide may be used without incurring a whitening effect, e.g., even up to 15% with acceptable whiteness, or possible higher.

Furthermore, our invention does not rely upon the use of hydrophilic titanium dioxide preparations as required in the above noted patent, nor are energy intensive processes as powder milling, nor are organic sunscreen actives required for the high efficacy.

The compositions of this invention are oil-in-water emulsions containing at least the following components:
 (a) an inorganic sunscreen agent, such as titanium dioxide or zinc oxide or a mixture thereof;
 (b) an anionic emulsifier; and
 (c) a carrier oil.

The compositions of this invention provide sunscreen formulations having and SPF of at least 10. They are easily made by simple mixing and provide an excellent dispersion of the inorganic sunscreen agent throughout the composition, thus ensuring even skin coverage. They are substantially invisible upon application to the skin.

DETAILED DESCRIPTION OF THE INVENTION

The sunscreen compositions of this invention yield highly effective ultraviolet- (UV) blocking capabilities; that is, a given level of protection is provided with a significantly lower concentration of titanium dioxide than previously obtained using commercially available powdered titanium dioxides. They do not require the unusual processing methods previously necessary to disperse the titanium dioxide into an oil, such as preparation of sub-batch mill bases, high shear mixing or milling, or applying such milling procedures to the final product formulation. Typical titanium dioxide sunscreen compositions of SPF 15 require levels of titanium dioxide that impart a significant whitening effect to the skin; the compositions of this invention, minimize this disadvantage.

The composition invented is an oil-in-water emulsion that is cosmetically superior to conventional inorganic sunscreen preparations, including water-in-oil titanium dioxide-only formulations, at equivalent SPF ratings, due to the low levels of titanium dioxide needed in the invention system. The compositions of this invention can be used for sun protection in daily wear or facial products as well as recreational situations. Because of the efficiency of the system, the inventive formulations are significantly lower in cost than other sunscreen systems.

There are several ingredients that contribute to the unexpectedly high efficiency of the compositions' blocking of UV radiation. These elements include the following materials:

The compositions of this invention should include one or more of a select group of anionic emulsifiers. In particular, certain salts of fatty acids are useful in the formulations of this invention. More particularly, the following anionic emulsifiers are useful in the compositions of this invention: sodium stearate, sodium laurate, sodium lauryl sulfate, DEA cetyl phosphate, dioctyl sulfosuccinate and the like. Most preferably, the emulsifier should be sodium stearate.

It is believed that straight-chain fatty acid salts, having relatively high melting points (about 70° C. or higher), are preferred due to their structure. For example, branched fatty acid salts are not as acceptable for use in the compositions of this invention. The anionic emulsifiers should be present in the compositions of this invention in an amount from about 0.01 to about 10%, more preferably 0.1 to about 7% and most preferably from about 0.5 to about 5%. There may be additional emulsifiers present in the compositions of this invention, such as nonionic emulsifiers known to those of ordinary skill in the art, such as sorbitan esters and ethoxylated sorbitan esters, ethoxylated fatty acids, fatty alcohols and ethoxylated fatty alcohols, fatty glyceride esters and ethoxylated fatty glyceride esters and the like. However, there should be at least one anionic emulsifier present in order to achieve the products of this invention. The fatty acid salt emulsifiers may be added to the composition in the salt, or the salt may be formed in situ.

A carrier oil should also be present in the compositions of this invention. Preferably, such carrier oils should be selected from the group of polyether interrupted fatty acid esters.

More preferably, the carrier oil should be a $C_8$ to $C_{22}$ fatty alkyl(optionally polypropylenoxy)polyethylenoxy, ether carboxylate ester, the ester having an alkyl group which has from one to twenty-two carbon atoms, optionally straight or branched. Most preferably, the carrier oil should be a isopropyl propylene glycol-2-isodeceth-7 carboxylate, such as Velsan D8P3 or other commercially available materials sold by Sandoz under the Velsan trade name. Preferably, the carrier oil should be present in the composition in an amount of between about 0.1% and about 10%. More preferably, it should be present in the amount of between about 1% and about 5%. Most preferably, it should be present in the amount of between about 2% and about 3%.

Preferably, the oil phase should contain at least two materials, the polyether carrier oil and a conventional emollient known to those of ordinary skill in the art as useful in sunscreen products, such as mineral oil, ester oils or others known to those of ordinary skill in the art, such as mineral oils, vegetable oils, silicones, synthetic emollients such as fatty acid esters and the like. This emollient should be present in the formulation in a ratio to the carrier concentration of from about 1:1 to about 3:1, most preferably, about 2:1. The carrier oil and the emollient should compose from about 2% to about 20% of the composition by weight.

The third element which should be present in the compositions of this invention is an inorganic sunscreen compound, such as titanium dioxide, zinc oxide or combinations thereof. Preferably, titanium dioxide should be used having a particle size from of less than about 300 nm in diameter. It should be present in the composition in the amount of from about 2% to about 25%. More preferably, it should be present in the amount of from about 2% to about 15%. Most preferably, it should be present in the amount of from about 3% to about 10%. The inorganic sunscreen compound should be oil dispersible, and may be present with or without surface coating.

The ratio of titanium dioxide to the weight of the carrier oil and the emollient combined should be from about 0.3:1 to about 1:1. Most preferably, the ratio should be about 0.5:1 and 2:3. For example, a composition containing 15% titanium dioxide, 8.33% Velsan D8P3, 12.5% Miglyol and the remainder of the composition identical to that of Example 1 below, results in a sunscreen composition having an SPF of 63. The whiteness value of this composition is acceptable and is only slightly whitening on the skin.

The pH of the compositions of this invention should be maintained at a level above about 5, more preferably, above about 5.5. Maintaining the pH at this level will ensure that the anionic emulsifier remains in the salt form, which is important in retaining the stability of the product.

Additionally, the usual elements of a modern sunscreen emulsion system, such as a polymeric thickener/stabilizer, one or more additional emollient oil, microbial preservatives, antioxidants, fragrance, humectant, and of course the water vehicle are utilized without known selection or restraint.

The compositions of this invention can be in either liquid or aerosol form. They can be incorporated into various cosmetic and personal care products such as hand and body lotions, oils, ointments, lip balm products, facial cosmetics and the like.

The sunscreen compositions of this invention may be prepared using one of at least two methods: a two-vessel method, in whcih the oil and water phases are individually prepared, and a one- vessel method into which all ingredients are added in selected, specific order. Any of these processes will produce a smooth, uniform, white to light ivory emulsion.

In accordance with the two-vessel process, a water phase is prepared by measuring deionized water into a beaker and mixing. The elements of the water phase, including emulsifiers and humectants, chelators, thickeners, waterproofing agents, neutralizing agents and antioxidants should be added and the solution heated. The anionic emulsifier may be placed into the water phase or into the oil phase, depending upon the nature of the emulsifier. The oil phase is prepared separately in another vessel, including the anionic emulsifier, carrier oil and inorganic sunscreen agent. The two phases are then held at a relatively high temperature and mixed.

More specifically, in the two-vessel process, water phase is prepared by measuring deionized water into a beaker and mixing. Next, Carbopol 940 should be added and the composition mixed until properly hydrated. Propylene glycol and EDTA should then be added and the composition mixed until a homogeneous solution is achieved. The solution should then be heated to 70–80° C. The solution should be maintained at 70–80° C. for phasing.

The oil phase is then prepared by adding the following ingredients into a beaker: BHT, Velsan D8P3, Stearic Acid, Cetyl Alcohol and Miglyol 812. The beaker should be placed in a water bath on an electric hot plate. The ingredients should be heated to about 80° C. or until melted. The titanium dioxide should be added slowly and the composition stirred at high speed until homogenous. The mixture should be maintained at about 80° C. until phasing.

The composition may then be phased by adding the Oil Phase to the Aqueous Phase and mixing, holding the temperature at about 80° C. for 5 minutes. Sodium hydroxide should then be added (as a 10% solution) and the composition mixed for 5 minutes at high speed. Next, the mixing speed should be reduced and cooling begun. When the temperature of the batch reaches 40–45° C., Dowicil 200 solution may be added and, optionally, fragrance. The pH should be checked and adjust to 8.00–8.50 with a 10% solution of Sodium Hydroxide, if needed (target pH 8.25). Deionized water may be added as required to bring the batch to final weight. When the temperature of the batch reaches 28–32° C., mixing and cooling may be discontinued.

In the one-vessel process, the water and oil phases may be made in the same vessel, provided that the components are added in an appropriate order. For example, the water phase should be created first, adding water and optionally certain emulsifiers which are compatible with the water phase to the vessel. The vessel should be heated to about 85° to about 95° C. Once the temperature reaches this level, the oil phase components may be added, including, optionally, the anionic emulsifier if it is oil-phase compatible and the carrier oil, as well as any additional oil-phase emulsifiers, antioxidants and emollients that may be desired. The temperature should be maintained at this level for about 15 minutes, and the inorganic sunscreen agent added slowly, and the composition mixed for a period of time of at least about 30 minutes. The pH may then be checked and adjusted to about 8.25, Dowicil, a preservative added as well as optional fragrance.

More specifically, deionized Water may be added to a beaker to which is slowly added Carbopol 940. Next, EDTA is added and the composition mixed at high speed for 15–20 minutes or until the Carbopol is properly hydrated. Heating of the mixture to 92–95° C. should be begun and the required amount of Propylene Glycol added during this time. When the temperature reaches 92–95° C., BHT, Velsan D8P3, Stearic Acid, Cetyl Alcohol and Miglyol 812 are added. The temperature of the mixture should be maintained at about 92–95° C. for about 15 minutes. Then, titanium dioxide should be added and the composition mixed for 30 minutes. Sodium Hydroxide (as a 10% solution) should be added and the composition mixed for 30 minutes at 88–92° C. The composition should be cooled and, at 40° C., Dowicil 200 solution added as well as optional fragrance. The pH should be adjusted to about 8–8.5 with Sodium Hydroxide (target pH is 8.25). Finally, sufficient water should be added to bring the batch to the target weight.

The following examples serve as illustrations of the compositions of this invention, however, they do not limit the scope of the invention described herein.

EXAMPLE 1

743.07 ml deionized water was added to a beaker. 2.5 grams Carbopol 940 (available from B. F. Goodrich of Cincinnati, Ohio) was then slowly added to the beaker. 1.0 gram Disodium EDTA was then added and the composition mixed at high speed for 15–20 minutes or until the Carbopol was properly hydratred. The mixture was heated to 92–95° C. and 30 grams of propylene glycol was added. When the temperature reached 92–95° C., 0.5 g BHT, 25 grams Velsan D8P-3 (available from Sandoz Corporation), 50 grams stearic acid, 10 grams cetyl alcohol and 37.5 grams Miglyol 812 (available from Huls Company of Piscataway, N.J.) were added. 45 grams titanium dioxide MT-100T, an aluminum stearate coated microfine titanium dioxide were then added to the vessel. Next, 49.93 grams of 10% solution sodium hydroxide were added and the composition mixed for 30 minutes at 88–92° C. Cooling began and when the composition reached 40° C. 3 grams Dowicil 200 ( a 33% solution of Quaternium 15) were added, as well as 2.5 grams of fragrance. The pH was adjusted to 8–8.5 with 49.93 grams of 10% solution of sodium hydroxide (target ph is 8.25). Finally, sufficient deionized water was added to bring the batch to the target weight.

The in-vitro SPF (Sun Protection Factor) of this composition was measured using the system described by Cole and VanFossen [Cole, C., VanFossen R., (1990) In-vitro model for UVB and UVA protection. In: Sunscreens: Development, Evaluation and Regulatory Aspects, N. Shaath and N. Lowe Eds., Marcel Dekker Pub. New York, N.Y.]. Briefly, this system consists of the measurement of transmission of solar simulated UV radiation through composition (1.2 mg/cm sup 2) applied to the skin. The system consists of an optical sensor that is only sensitive to sunburning radiation and has a sensitivity spectrum similar to the human erythema sensitivity spectrum. The SPF is the ratio of the optical signal through excised mouse skin without sunscreen divided by the optical signal through the excised mouse skin with the sunscreen. The system is calibrated against a series of sunscreens of known SPF (4 through 36) determined in-vivo using the FDA monograph method (Federal Register, Aug. 25, 1978, Sunscreen drug products for over-the-counter human drugs. pp 38206–38269.) The resulting SPF of the composition of Example I above is 16.9 and the composition is aesthetically satisfactory and stable.

EXAMPLES 2–14

In the next series of examples the use of titanium dioxides of different origins and/or types of coating at the same concentration of 4.5% was investigated. The compositions were all made in accordance with the method set forth in Example 1, having the same components in the same concentrations but for the varied component. The results are set forth in Table I.

TABLE I

Effect of TiO$_2$ Coating on the SPF (4.5% TiO$_2$)

| (2)TiO$_2$ Source | Surface Treatment | SPF |
|---|---|---|
| (3)MT-100T (Tri-K Industries, Inc.) | Al, Stearic Acid | 16.9 |
| (4)MT-500T (Tri-K Industries, Inc.) | None | 13.6 9.9 |
| (5)SMT-100SAS (Tri-K Industries, Inc.) | Methyl hydrogen polysiloxane | 5.0 |
| (6)UV Than M262 (Presperse, Inc.) | Alumina, Dimethicone | 18.0 12.0 |
| (7)UV Titan M212 (Presperse, Inc.) | Alumina, Glycerin | 8.5 |
| (8)P25 (Degussa) | None | 9.1 |
| (9)STT65C-S (Kobo) | None | 12.1 |
| (10)DM140 KSI (Kobo) | STT65C-S surface treated with silicone | 11.5 |
| (11)STT-30D-S (Kobo) | Al, Si, Silicone | 3.8 |
| (12)STT-30S-L (Kobo) | Al, Stearic Acid | 7.3 |
| (13)TiO$_2$ (Hydrophobic) Creative Polymers | Methicone, Dimethicone | 12.0 |
| (14)TiO$_2$ (Hydrophilic) Creative Polymers | Dimethicone Copolyol | 7.7 |

EXAMPLES 15–17

In this series of examples the concentration of titanium dioxide was varied and the resulting SPF was measured. The formulae are made in accordance with the method set forth in Example 1 and differ in concentration only as to the amount of titanium dioxide. The difference was made up with deionized water.

| MT-100T Titanium dioxide concentration | SPF |
|---|---|
| (15) 4.5% | 17.1 |
| (16) 6.0% | 25.3 |
| (17) 7.5% | 20.4 |

EXAMPLES 18–21

The following examples are intended to show which anionic emulsifiers result in a high SPF. The compositions were identical to that of Example, except in that the anionic emulsifier was varied in accordance with the information set forth in Table II below. From the data presented in the Table II, it can be seen that dioctylsulfosuccinate, DEA cetyl phosphate (Amphisol) under the right circumstances, Sodium lauryl sulfate and sodium stearate are all effective in yielding an SPF higher than 10.

TABLE II

Effect of Anionic Emulsifiers on the SPF

| | PF |
|---|---|
| (18)Sodium Stearate (NaOH Neut.)-Staeric acid plus Sodium Hydroxide | 11.6 |
| (19)sodium stearate in water phase | 15.7 |
| (20)5.0% Isostearic Acid no Brij 721, no Stearic Acid with Miglyol 812 and Velsan D8P-3 | 4.5 |
| (21)5.0% Isostearic Acid (added to H₂O + NaOH) 3.0% Brij 721 | 8.6 |
| (22)5.0% Oleic Acid, no Stearic Acid, pH adj. | 6.1 |
| | 5.2 |
| (23)5.0% Laurie Acid, no stearic Acid | 6.4 |
| (24)2.0% Amphisol with 3.0% Brij 721 and Stearic Acid, no pH adj. | 12.3 |
| (25)2.0% Amphisol with Brij 721 and no Stearic Acid | 8.1 |
| (26)2.0% Amphisol with Brij 721 and Beeswax, no Stearic Acid, no pH adjust | 15.1 |
| (27)0.5% Sodium Lauryl Sulfate with Stearic Acid, 3.0% Brij 721, no pH adj. | 15.0 |
| (28)1.0% Lecithin, no Stearic Acid 3.0% Brij 721, no pH adj. | 3.0 |
| (29)Aerosol OT-75 with Stearic Acid, Brij 721, pH not adjusted | 11.2 |
| (30)Aerosol OT-75 with Stearic Acid, Brij 721, pH not adjusted plus 0.5% Na Stearate | 16.2 |
| (31)Hamposyl C-30, no stearic acid | 5.9 |

The brandnames set forth above refer to the following compounds:
Brig 721: Non ionic surfactant: Polyoxyethylene 21 stearyl ether
Miglyol 812: Capric/caprylic triglyceride
Velsan D8P-3: Isopropyl propylene glycol-2-isodeceth-7 carboxylate
Amphisol: DEA Cetyl phosphate
Aerosol OT-75: Dioctyl sodium sulfosuccinate
Hampocyl is a sodium cocoylsarcosinate, an anionic emulsifier

EXAMPLES 32–43

The following examples 32–43 demonstrate that, unless sodium stearate, an anionic emulsifier, is present, non ionic emulsifiers do not result in a high SPF. The compositions set forth below are identical to that of Example 1 except for the variations indicated in Table III below.

TABLE III

Effect of Nonionic Emulsifier on the SPF

| | SPF |
|---|---|
| (32)6.0% Cetyl Alcohol, no Stearic Acid 3.0% Brij 721, and no pH adj. | 2.7 |
| (33)5.0% Glycetyl Monostearate, 2.0% Tween 60, 1.0% Arlacel 60, no Stearic Acid, pH = 7 | 2.9 |
| (34)5.0% Glycetyl Monostearate, 3.0% Brij 721, no Stearic acid | 5.1 |
| (35)2.7% Brij 721/0.3% Brij 72, no Stearic Acid, pH 7 | 2.5 |
| (36)2.7% Brij 721/0.3% Brij 72 and 0.5% Rewoderm S1333, no Stearic Acid pH 7 | 4.1 |
| (37)2.7% Tween 60/0.3% Span 60, no Stearic Acid, pH 7 | 3.6 |
| (38)2.7% Tween 60/0.3% Span 60 and 0.5% Rewoderm S1333, no Stearic Acid, pH 7 | 4.2 |
| (39) 3.0% Glucam E-20 Distearate, no Stearic Acid | 2.9 |
| (40)3.0% Glucam E-20 Distearate and 0.5% Rewoderm S1333, no Stearic Acid, pH 7 | 3.8 |
| (41)3.0% Glucam SSE-20, no Stearic Acid | 3.3 |
| (42)3.0% Glucam SSE-20 and 0.5% Rewoderm S1333, no Stearic Acid, pH 7 | 3.5 |
| (43)5.0% Glucam P-20, no Stearic Acid, | 2.5 |

TABLE III-continued

Effect of Nonionic Emulsifier on the SPF

| | SPF |
|---|---|

Tween 60 is a polyoxyethylene (20) sorbitan monostearate.
Arlacel 60 is a sorbitan monostearate.
Arlacel 165 is a glycerol monostearate and polyoxyethylene stearate.
Span 60 is a sorbitan monostearate.
Rewoderm S-1333 is an anionic polyfunctional surfactant.
Glucam E-20 distearate is a methylgluceth 20 distearate.
Glucam SSE-20 is an ethoxylated (20) methyl glucoside sequistearate.

EXAMPLES 44–91

The following Examples 44- set forth the importance of using carrier oils in the products of this invention in conjunction with emollient oils known to those of ordinary skill in the art and available commercially. They are similar to Example 1, varying only the oil component, as indicated below.

| Effect of Single Oils and Oil mixtures | |
|---|---|
| (45)Finsolv TN (6.25%) | 7.0 |
| (46)Finsolv TN(2.5%)/Miglyol 812 (3.75%) | 15.8 |
| (47)Finsolv TN(3.75%)/Velsan D8P-3(2.5%) | 16.4 (4.1), 18.4 (4.4) |
| (48)3.125% Finsolv TN/3.125% Mineral Oil NF | 9.1 (3.2) |
| (49)3.125% Finsolv TN/3.125% Cetiol 868 | 8.2 (2.9) |
| (50)Miglyol 812(6.25%) | 8.9 (3.2) |
| (51)Velsan D8P-3(6.25%) | 10.0 (3.3) |
| (52)Procetyl AWS(6.25%) | 9.9 (3.4) |
| (53)Procetyl AWS(3.75%)/Velsan D8P-3(3.25%) | 16.8 (4.2) |
| (54)Procetyl AWS(3.75%)/Miglyol 812(2.5%) | 10.6 (3.3) |
| (55)3.125% Procetyl AWS/3.125% Mineral Oil NF | 10.7 (3.2) |
| (56)3.125% Procetyl AWS/3.125% Citmol 316 | 11.6 (3.5) |
| (57)Isopropyl Myristate(6.25%) | 8.7 (2.8), 5.3 (2.4) |
| (58)Isopropyl Myristate(3.75%), 2.5% Velsan D8P-3 | 13.0 (3.4) |
| (59)Cetiol 868 (Octyl Stearate)7/25% | 8.7 (3.0) |
| (60)Cetiol 868(3.75%), 2.5% Velsan D8P-3 | 14.2 (3.7) |
| (61)Mineral Oil, NF(6.25%) | 6.7 (2.8) |
| (62)Mineral Oil, NF(3.75%), 2.5% Velsan D8P-3 | 15.2 (3.8) |
| (63)3.125% Mineral Oil, NF 3.125% Citmol 316 | 4.3 (2.4) |
| (64)3.125% Mineral Oil, NF 3.125% Minno 21 | 4.6 (2.1) |
| (65)Drakeol-7 (2.5 %)/Miglyol 812(3.75%) | 6.9 (2.9) |
| (66)Klearol (5.0%) | 11.0 (3.4) |
| (67)Klearol (2.5%)/Miglyol 812(3.75%) | 6.6 (2.9), 5.4 (2.6), 7.0 (3.2), 7.7 (2.5) |
| (68)Arlamol E(6.25%) | 5.3 (2.2) |
| (69)Arlamol E(3.75%), 2.5% Velsan D8P-3 | 14.3 (3.4) |
| (70)Dimethicone(6.25%) | 7.3 (3.0) |
| (71)3.75% Dimethicone, 2.5% Velsan D8P-3 | 14.1 (3.7) |
| (72)2.5% Dimethicone, 3.75% Miglyol 812 | 3.5 (2.0) |
| (73)3.0% Miglyol 812, 2.5% Velsan D8P-3 Stearic Acid | 15.1 (3.5) 11.8 (2.8) |
| (73A)2.5% Eumulgin L, no Velsan D8P-3 | |
| (74)6.25% Eumulgin L, no Velsan D8P-3, no Miglyol 812 | 11.2 (3.6) |
| (75)2.5% Crodamol ML, no Velsan D8P-3 | 10.4 (3.0) |
| (76)2.5% Hetester PHA | 13.1 (3.4) |
| (77)2.5% Procetyl 10 | 9.5 (3.0) |
| (78)2.5% Marlox FK86 | 11.0 (3.0) |
| (79)2.5% Ucon 50 HB-660 | 9.4 (2.8) |
| (80)2.5% Eumulgin B-2 | 12.5 (3.2) |
| (81)6.25% Eumulgin B-2 | 9.3 (3.0) |
| (82)2.5% Avanel S150, no Velsan, 3.75 Miglyol | 5.1 (2.3) |
| (83)2.0% Avanel S150, no Stearic Acid, 2.5% Velsan and 3.75% Miglyol and 3% Brij 721 | 3.2 (2.0) |

-continued

| Effect of Single Oils and Oil mixtures | |
|---|---|
| (84) 5.74% Avanel S150, no Velsan, no Miglyol | 7.0 (2.6) |
| (85) 2.5% Sandoxylate 424 | 13.0 (3.4) |
| (86) 2.5% Sandoxylate 418 | 12.8 (3.1) |
| (87) 2.5% Sandoxylate 412 | 16.0 (3.3) |
| (88) 2.5% Sandoxylate 408 | 15.1 (3.3) |
| (89) 2.5% UCON 50 HB-660 | 9.4 (2.8) |
| (90) 2.5% Velsan P8-3 | 11.0 (3.0) |
| (91) 3.0% Miglyol 812, 2.5% Velsan D8P-3, Stearic Acid | 15.1 (3.5) |

EXAMPLES 91–94

In the following examples 91–94, the type of Velsan material was varied. Otherwise, the compositions are identical to that of Example 1.

| Effect of Velsan Type* on the SPF (with Constant Miglyol 812 3.75%) | |
|---|---|
| (91) Velsan D8P-3 | 15.3 (3.3) |
|  | 21.0 (4.2) |
| (92) Velsan D8P-16 (paste) | 12.6 (3.0) |
| (93) Velsan D8P-16 (liquid) | 14.0 (3.4) |
| (94) Velsan P8-3 (liquid) | 14.0 (3.3) |

*Velsan D8P-3 level was 2.5%

EXAMPLE 95

A composition for use as a sunscreen was made, having components identical to those of Example 1, but in the oil phase was added 3% of octylmethoxycinnamate and the water adjusted down 3%. The resulting composition had an SPF of 23.3. Thus, it can be seen that the compositions of this invention may include organic as well as inorganic sunscreen agents.

EXAMPLE 96

A composition for use as a sunscreen was made, having components identical to those of Example 1, 5% of zinc oxide and 3% of Brij 721 were added. The resulting composition had an SPF of 20.4. The pH of the composition was adjusted to 7. This composition has a significantly enhanced protection value in UVA.

What is claimed is:

1. A sunscreen composition comprising:
   (a) an inorganic sunscreen agent;
   (b) an anionic emulsifier; and
   (c) an oil component comprising a carrier oil and at least one emollient, wherein said carrier oil is a polyether interrupted fatty acid ester.

2. A sunscreen composition according to claim 1 wherein said inorganic sunscreen agent is selected from the group consisting of titanium dioxide, zinc oxide and mixtures thereof.

3. A sunscreen composition according to claim 2 wherein said inorganic sunscreen agent is titanium dioxide.

4. A sunscreen composition according to claim 3 wherein said titanium dioxide has a particle size of less than about 30 nanometers.

5. A sunscreen composition according to claim 1 wherein said anionic emulsifier is a salt of a fatty acid.

6. A sunscreen composition according to claim 1 wherein said anionic emulsifier is selected from the group of sodium stearate, sodium laurate, sodium lauryl sulfate, DEA cetyl phosphate, and dioctyl sulfosuccinate.

7. A sunscreen composition according to claim 1 wherein said polyether interrupted fatty acid ester is a $C_8$ to $C_{22}$ fatty alkyl(optionally polypropylenoxy)polyethylenoxy, ether carboxylate ester, the ester having an alkyl group which has from one to twenty-two carbon atoms, optionally straight or branched.

8. A sunscreen composition according to claim 1 wherein said composition further comprises nonionic emulsifiers or mixtures thereof.

9. A sunscreen composition according to claim 1 wherein said composition has a pH of at least 5.

10. A sunscreen composition according to claim 9 wherein said pH is from about 7.5 to about 8.5.

11. A sunscreen composition according to claim 1 having a Sun Protection Factor of at least 10.

12. A method of making a sunscreen composition comprising:
   (a) adding deionized water to a vessel;
   (b) then, heating the water;
   (c) then, adding a carrier oil and an anionic surfactant to the vessel;
   (d) then, slowly adding an inorganic sunscreen agent to said vessel and heating and mixing said resultant composition; and
   (e) then, adjusting the pH of said composition to above 5.

13. A sunscreen composition comprising from about 2% to about 25% of an inorganic sunscreen agent, from about 0.5% to about 10% of an anionic surfactant and from about 0.5 to about 10% of an oil component comprising a carrier oil and an emollient, wherein said carrier oil is a polyether interrupted fatty acid ester.

14. A sunscreen composition according to claim 1 wherein the ratio of inorganic sunscreen agent to oil component is from about 0.3:1 to about 1:1.

* * * * *